US007105294B2

(12) United States Patent
Van Dongen et al.

(10) Patent No.: US 7,105,294 B2
(45) Date of Patent: *Sep. 12, 2006

(54) METHOD AND PROBES FOR THE DETECTION OF CHROMOSOME ABERRATIONS

(75) Inventors: Jacobus Johannus Maria Van Dongen, Niewekerk Aan De Ijssel (NL); Karl-Johan Pluzek, Smorum (DK); Kirsten Vang Nielsen, Bronshoj (DK); Kim Adelhorst, Holte (DK)

(73) Assignee: Dako Denmark A/S, Glostrup (DK)

( * ) Notice: Subject to any disclaimer, the term of this patent is extended or adjusted under 35 U.S.C. 154(b) by 345 days.

This patent is subject to a terminal disclaimer.

(21) Appl. No.: 10/229,110

(22) Filed: Aug. 27, 2002

(65) Prior Publication Data

US 2004/0043383 A1    Mar. 4, 2004

Related U.S. Application Data

(63) Continuation of application No. 09/674,792, filed as application No. PCT/DK99/00245 on May 4, 1999, now abandoned.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3; 536/24.33

(58) Field of Classification Search .................... 435/6; 536/23.1, 24.3, 24.33
See application file for complete search history.

(56) References Cited

U.S. PATENT DOCUMENTS

| | | | |
|---|---|---|---|
| 4,681,840 A | 7/1987 | Stephenson et al. |
| 4,707,440 A | 11/1987 | Stavrianopoulos |
| 4,755,458 A | 7/1988 | Rabbani et al. |
| 4,843,122 A | 6/1989 | Stavrianopoulos |
| 4,849,208 A | 7/1989 | Stavrianopoulos |
| 4,849,505 A | 7/1989 | Stavrianopoulos |
| 4,868,103 A | 9/1989 | Stavrianopoulos et al. |
| 4,892,817 A | 1/1990 | Pawlak |
| 4,912,034 A | 3/1990 | Kalra et al. |
| 4,943,523 A | 7/1990 | Stavrianopoulos |
| 4,952,685 A | 8/1990 | Stavrianopoulos |
| 4,968,603 A | 11/1990 | Slamon et al. |
| 4,994,373 A | 2/1991 | Stavrianopoulos et al. |
| 5,013,831 A | 5/1991 | Stavrianopoulos |
| 5,015,568 A | 5/1991 | Tsujimoto et al. |
| 5,079,147 A | 1/1992 | Showe et al. |
| 5,082,783 A | 1/1992 | Ernst et al. |
| 5,149,628 A | 9/1992 | Croce |
| 5,175,269 A | 12/1992 | Stavrianopoulos |
| 5,198,338 A | 3/1993 | Croce |
| 5,241,060 A | 8/1993 | Engelhardt et al. |
| 5,242,795 A | 9/1993 | Croco |
| 5,244,787 A | 9/1993 | Key et al. |
| 5,258,507 A | 11/1993 | Cruickshank et al. |
| 5,260,433 A | 11/1993 | Engelhardt et al. |
| 5,369,008 A | 11/1994 | Arlinghaus et al. |
| 5,439,649 A | 8/1995 | Tseung et al. |
| 5,447,841 A | 9/1995 | Gray et al. |
| 5,472,842 A | 12/1995 | Stokke et al. |
| 5,487,970 A | 1/1996 | Rowley et al. |
| 5,491,224 A | 2/1996 | Bittner et al. |
| 5,492,837 A | 2/1996 | Naser-Kolahzadeh et al. |
| 5,506,350 A | 4/1996 | Bittner et al. |
| 5,512,433 A | 4/1996 | Cruickshank et al. |
| 5,529,925 A | 6/1996 | Morris et al. |
| 5,538,846 A | 7/1996 | Meeker |
| 5,538,869 A | 7/1996 | Siciliano et al. |
| 5,547,838 A | 8/1996 | Nisson et al. |
| 5,567,586 A | 10/1996 | Croce |
| RE35,491 E | 4/1997 | Cline et al. |
| 5,622,829 A | 4/1997 | King et al. |
| 5,633,135 A | 5/1997 | Croce et al. |
| 5,633,136 A | 5/1997 | Croce et al. |
| 5,633,365 A | 5/1997 | Stokke et al. |
| 5,639,602 A | 6/1997 | Rashtchian et al. |
| 5,648,481 A | 7/1997 | Parodos et al. |
| 5,663,319 A | 9/1997 | Bittner et al. |
| 5,665,549 A | 9/1997 | Pinkel et al. |
| 5,677,130 A | 10/1997 | Meeker |
| 5,679,517 A | 10/1997 | Evans et al. |

(Continued)

FOREIGN PATENT DOCUMENTS

DE        19610255 A1        9/1997

(Continued)

OTHER PUBLICATIONS

Egholm, Michael et al., "PNA hybridizes to complementary oligonucleotides obeying the Watson-Crick hydrogen-bonding rules," *Nature*, 365:566-568 (1993).

(Continued)

*Primary Examiner*—Jezia Riley
(74) *Attorney, Agent, or Firm*—Finnegan, Henderson, Farabow, Garrett & Dunner, LLP

(57) ABSTRACT

A novel method for detecting chromosome aberrations is disclosed. More specifically, chromosome aberrations are detected by in situ hybridisation using at least two sets of hybridisation probes, at least one set comprising one or more peptide nucleic acid probes capable of hybridising to specific nucleic acid sequences related to a potential aberration in a chromosome, and at least one set comprising two or more peptide nucleic acid probes capable of hybridising to specific nucleic acid sequences related to another potential aberration in a chromosome. In particular, the method may be used for detecting chromosome aberrations in the form of breakpoints.

19 Claims, No Drawings

U.S. PATENT DOCUMENTS

| | | |
|---|---|---|
| 5,684,142 A | 11/1997 | Mishra et al. |
| 5,693,464 A | 12/1997 | Trent et al. |
| 5,695,976 A | 12/1997 | Jørgensen et al. |
| 5,698,398 A | 12/1997 | Shassere et al. |
| 5,700,921 A | 12/1997 | Westling et al. |
| 5,721,098 A | 2/1998 | Pinkel et al. |
| 5,731,153 A | 3/1998 | Lucas et al. |
| 5,750,400 A | 5/1998 | Murphy et al. |
| 5,756,294 A | 5/1998 | White et al. |
| 5,756,696 A | 5/1998 | Gray et al. |
| 5,759,781 A | 6/1998 | Ward et al. |
| 5,770,421 A | 6/1998 | Morris et al. |
| 5,776,688 A | 7/1998 | Bittner et al. |
| 5,786,181 A | 7/1998 | Stassi et al. |
| 5,789,161 A | 8/1998 | Morrison et al. |
| 5,801,021 A | 9/1998 | Gray et al. |
| 5,804,384 A | 9/1998 | Müller et al. |
| 5,808,026 A | 9/1998 | Cohen et al. |
| 5,821,328 A | 10/1998 | King et al. |
| 5,824,478 A | 10/1998 | Müller |
| 5,837,466 A | 11/1998 | Lane et al. |
| 5,846,749 A | 12/1998 | Slamon et al. |
| 5,854,409 A | 12/1998 | Westling et al. |
| 5,856,089 A | 1/1999 | Wang et al. |
| 5,856,097 A | 1/1999 | Pinkel et al. |
| 5,858,663 A | 1/1999 | Nisson et al. |
| 5,888,733 A | 3/1999 | Hyldig-Nielsen et al. |
| 5,888,734 A | 3/1999 | Cremer et al. |
| 5,892,010 A | 4/1999 | Gray et al. |
| 5,922,543 A | 7/1999 | Cremer |
| 5,925,519 A | 7/1999 | Jensen et al. |
| 5,939,265 A | 8/1999 | Cohen et al. |
| 5,955,367 A | 9/1999 | Adams et al. |
| 5,958,681 A | 9/1999 | Wetmur et al. |
| 5,965,362 A | 10/1999 | Pinkel et al. |
| 5,968,734 A | 10/1999 | Aurias et al. |
| 5,976,790 A | 11/1999 | Pinkel et al. |
| 5,994,071 A | 11/1999 | Ross et al. |
| 5,994,076 A | 11/1999 | Chenchik et al. |
| 5,998,135 A | 12/1999 | Rabbani et al. |
| 6,005,095 A | 12/1999 | Capaccioli et al. |
| 6,007,994 A | 12/1999 | Ward et al. |
| 6,025,126 A | 2/2000 | Westbrook |
| 6,037,129 A | 3/2000 | Cole et al. |
| 6,040,140 A | 3/2000 | Croce et al. |
| 6,083,709 A | 7/2000 | Reynolds et al. |
| 6,100,029 A | 8/2000 | Lapidus et al. |
| 6,121,419 A | 9/2000 | Rowley et al. |
| 6,127,118 A | 10/2000 | Meeker |
| 6,132,961 A | 10/2000 | Gray et al. |
| 6,150,110 A | 11/2000 | Fletcher et al. |
| 6,159,685 A | 12/2000 | Pinkel et al. |
| 6,174,674 B1 | 1/2001 | Morris et al. |
| 6,174,681 B1 | 1/2001 | Halling et al. |
| 6,203,977 B1 | 3/2001 | Ward et al. |
| 6,214,558 B1 | 4/2001 | Shuber et al. |
| 6,218,529 B1 | 4/2001 | An et al. |
| 6,221,607 B1 | 4/2001 | Tsipouras et al. |
| 6,239,271 B1 | 5/2001 | Rabbani et al. |
| 6,251,601 B1 | 6/2001 | Bao et al. |
| 6,255,465 B1 | 7/2001 | Ferguson-Smith et al. |
| 6,268,184 B1 | 7/2001 | Gray et al. |
| 6,270,760 B1 | 8/2001 | Adams et al. |
| 6,270,971 B1 | 8/2001 | Ferguson-Smith et al. |
| 6,277,569 B1 | 8/2001 | Bittner et al. |
| 6,280,721 B1 | 8/2001 | Adams et al. |
| 6,280,929 B1 | 8/2001 | Gray et al. |
| 6,284,882 B1 | 9/2001 | Wu-Wong et al. |
| 6,335,167 B1 | 1/2002 | Pinkel et al. |
| 6,344,315 B1 | 2/2002 | Gray et al. |
| 6,352,829 B1 | 3/2002 | Chenchik et al. |
| 6,358,682 B1 | 3/2002 | Jaffee et al. |
| 6,358,685 B1 | 3/2002 | Wetmur et al. |
| 6,368,791 B1 | 4/2002 | Felix et al. |
| 6,376,188 B1 | 4/2002 | Halling et al. |
| 6,391,592 B1 | 5/2002 | Su et al. |
| 6,414,133 B1 | 7/2002 | Dietz-Band et al. |
| 6,429,303 B1 | 8/2002 | Green et al. |
| 6,451,529 B1 | 9/2002 | Jensen et al. |
| 6,451,551 B1 | 9/2002 | Zhan et al. |
| 6,451,997 B1 | 9/2002 | Morris et al. |
| 6,475,720 B1 | 11/2002 | Gray et al. |
| 6,489,455 B1 | 12/2002 | Chenchik et al. |
| 6,500,612 B1 | 12/2002 | Gray et al. |
| 6,506,563 B1 | 1/2003 | Ward et al. |
| 6,514,693 B1 | 2/2003 | Lansdorp |
| 6,544,784 B1 | 4/2003 | Bullerdiek et al. |
| 6,548,259 B1 | 4/2003 | Ward et al. |
| 6,566,058 B1 | 5/2003 | Cardy |
| 6,566,068 B1 | 5/2003 | Rabbani et al. |
| 6,569,626 B1 | 5/2003 | Bittner et al. |
| 6,573,042 B1 | 6/2003 | Wang |
| 6,573,043 B1 | 6/2003 | Cohen et al. |
| 6,576,421 B1 | 6/2003 | Westbrook |
| 6,607,877 B1 | 8/2003 | Gray et al. |
| 6,610,498 B1 | 8/2003 | Berendes et al. |
| 6,686,165 B1 | 2/2004 | van Dongen et al. |
| 6,689,875 B1 | 2/2004 | Dierlamm et al. |
| 6,730,474 B1 * | 5/2004 | van Dongen et al. ........... 435/6 |
| 6,770,477 B1 | 8/2004 | Slamon et al. |
| 6,808,878 B1 | 10/2004 | Gray et al. |
| 2001/0026921 A1 | 10/2001 | Rabbani et al. |
| 2002/0009720 A1 | 1/2002 | Van De Ven et al. |
| 2002/0019001 A1 | 2/2002 | Light |
| 2002/0028460 A1 | 3/2002 | Pinkel et al. |
| 2002/0042056 A1 | 4/2002 | van Dongen et al. |
| 2002/0098510 A1 | 7/2002 | Su et al. |
| 2002/0132246 A1 | 9/2002 | Kallioniemi et al. |
| 2002/0138857 A1 | 9/2002 | Ghayur |
| 2002/0160409 A1 | 10/2002 | Halling et al. |
| 2002/0177130 A1 | 11/2002 | Gray et al. |
| 2002/0182586 A1 | 12/2002 | Morris et al. |
| 2002/0182628 A1 | 12/2002 | Dietz-Band et al. |
| 2002/0182701 A1 | 12/2002 | Chang et al. |
| 2002/0192692 A1 | 12/2002 | Palanisamy et al. |
| 2003/0021813 A1 | 1/2003 | Chovan et al. |
| 2003/0022178 A1 | 1/2003 | Schneewind et al. |
| 2003/0027752 A1 | 2/2003 | Steward et al. |
| 2003/0039658 A1 | 2/2003 | Estable et al. |
| 2003/0039966 A1 | 2/2003 | Hering et al. |
| 2003/0040005 A1 | 2/2003 | Jensen et al. |
| 2003/0059790 A1 | 3/2003 | Jaffee et al. |
| 2003/0087248 A1 | 5/2003 | Morrison et al. |
| 2003/0087865 A1 | 5/2003 | Golub et al. |
| 2003/0096255 A1 | 5/2003 | Felix et al. |
| 2003/0099987 A1 | 5/2003 | Westbrook |
| 2003/0108943 A1 | 6/2003 | Gray et al. |
| 2003/0124563 A1 | 7/2003 | Gerdes |
| 2003/0124629 A1 | 7/2003 | Tse et al. |
| 2003/0129626 A1 | 7/2003 | Nielsen |
| 2003/0143524 A1 | 7/2003 | Lemer |
| 2003/0148270 A1 | 8/2003 | Gray et al. |
| 2003/0148382 A1 | 8/2003 | Sun et al. |
| 2003/0152987 A1 | 8/2003 | Cohen et al. |
| 2003/0157527 A1 | 8/2003 | Lastrucci |
| 2003/0176682 A1 | 9/2003 | Dierlamm et al. |
| 2003/0190654 A1 | 10/2003 | Heidenreich et al. |
| 2003/0198977 A1 | 10/2003 | Nolan et al. |
| 2003/0235840 A1 | 12/2003 | Ward et al. |
| 2004/0009493 A1 | 1/2004 | Mohammed et al. |
| 2004/0029142 A1 | 2/2004 | Schon |
| 2004/0072188 A1 | 4/2004 | Ambrose et al. |
| 2004/0096872 A1 | 5/2004 | Gray et al. |
| 2004/0110227 A1 | 6/2004 | Levanon et al. |

| | | | |
|---|---|---|---|
| 2004/0180349 A1 | 9/2004 | Kaye et al. | |
| 2004/0235039 A1 | 11/2004 | Gray et al. | |
| 2005/0118634 A1 | 6/2005 | Pinkel et al. | |
| 2005/0137389 A1 | 6/2005 | Gray et al. | |

FOREIGN PATENT DOCUMENTS

| | | |
|---|---|---|
| EP | 0 181 635 | 5/1986 |
| EP | 0 500 290 A2 | 8/1992 |
| EP | 0 727 487 | 8/1996 |
| EP | 0727487 A1 | 8/1996 |
| EP | 0 549 709 B1 | 1/1997 |
| EP | 0825198 A1 | 2/1998 |
| EP | 0878552 A1 | 11/1998 |
| EP | 0 885 971 A2 | 12/1998 |
| EP | 0 430 402 B1 | 1/1999 |
| EP | 0 558 732 B1 | 3/1999 |
| EP | 0 631 635 B1 | 9/2001 |
| EP | 1 134 293 A2 | 9/2001 |
| EP | 1 146 892 B1 | 8/2003 |
| EP | 1 365 033 A1 | 11/2003 |
| EP | 1 369 482 A1 | 12/2003 |
| EP | 0 787 805 A3 | 1/2004 |
| EP | 1 388 589 A1 | 2/2004 |
| EP | 1 314 980 A3 | 3/2004 |
| EP | 1 394 715 A1 | 3/2004 |
| EP | 1 362 929 A3 | 5/2004 |
| EP | 1 415 659 A2 | 5/2004 |
| EP | 1 422 524 A1 | 5/2004 |
| WO | WO 89/11101 | 11/1989 |
| WO | WO 90/05789 | 5/1990 |
| WO | WO 91/07489 | 5/1991 |
| WO | WO 91/09129 | 6/1991 |
| WO | WO 91/13172 | 9/1991 |
| WO | WO 92/00311 | 1/1992 |
| WO | WO 92/16662 | 10/1992 |
| WO | WO 93/03187 | 2/1993 |
| WO | WO 93/06245 | 4/1993 |
| WO | WO 93/11265 | 6/1993 |
| WO | WO 93/17128 | 9/1993 |
| WO | WO 93/24652 | 12/1993 |
| WO | WO 93/24653 | 12/1993 |
| WO | WO 94/06812 | 3/1994 |
| WO | WO 94/06936 | 3/1994 |
| WO | WO 94/09022 | 4/1994 |
| WO | WO 94/24308 | 10/1994 |
| WO | WO 95/13398 | 5/1995 |
| WO | WO 95/17430 | 6/1995 |
| WO | WO 95/31545 | 11/1995 |
| WO | WO 96/00234 | 1/1996 |
| WO | WO 96/17958 | 6/1996 |
| WO | WO 96/18906 | 6/1996 |
| WO | WO 97/18325 | 5/1997 |
| WO | WO 98/37231 | 8/1998 |
| WO | WO 98/49275 | 11/1998 |
| WO | WO 98/51817 | 11/1998 |
| WO | WO 99/00520 | 1/1999 |
| WO | WO 99/51961 | 10/1999 |
| WO | WO 99/63342 | 12/1999 |
| WO | WO 00/06773 | 2/2000 |
| WO | WO 00/24940 | 5/2000 |
| WO | WO 00/32810 | 6/2000 |
| WO | WO 00/60119 | 10/2000 |
| WO | WO 01/06001 | 1/2001 |
| WO | WO 01/20027 | 3/2001 |
| WO | WO 01/20033 | 3/2001 |
| WO | WO 01/23621 | 4/2001 |
| WO | WO 01/29265 | 4/2001 |
| WO | WO 01/40301 | 6/2001 |
| WO | WO 01/66776 | 9/2001 |
| WO | WO 01/75160 | 10/2001 |
| WO | WO 01/88500 | 11/2001 |
| WO | WO 02/18601 | 3/2002 |
| WO | WO 02/28900 | 4/2002 |
| WO | WO 02/44411 | 6/2002 |
| WO | WO 03/33668 | 4/2003 |
| WO | WO 03/39438 | 5/2003 |
| WO | WO 03/40366 | 5/2003 |
| WO | WO 03/54207 | 7/2003 |
| WO | WO 03/66898 | 8/2003 |

OTHER PUBLICATIONS

Kosynkina, Larisa et al., "A Convenient Synthesis of Chiral Peptide Nucleic Acid (PNA) Monomers," *Tetrahedron Letters*, 35(29) :5173-5176 (1994).

Roberts, Christopher et al., "Synthesis of Oligonucleotides Bearing the Non-Standard Bases iso-C and iso-G. Comparison of iso-C-iso-G, C-G and U-A Base-Pair Stabilities in RNA/DNA Duplexes," *Tetrahedron Letters*, 36(21) :3601-3604 (1995).

Lichter et al., "Rapid Detection of Human Chromosome 21 Aberrations by In Situ Hybridization," Proc. Natl. Acad. Sci. USA, vol. 85, pp. 9664-9668, Dec. 1988.

Cremer et al., "Rapid Interphase and Metaphase Assessment of Specific Chromosomal Changes in Neuroectodermal Tumor Cells by In Situ Hybridization with Chemically Modified DNA Probes," Exp. Cell Res., vol. 176, pp. 199-220, 1988.

Trask et al., "Fluorescence In Situ Hybridization to Interphase Cell Nuclei in Suspension Allows Flow Cytometric Analysis of Chromosome Content and Microscopic Analysis of Nuclear Organization," Hum. Genet., vol. 78, pp. 251-259, Mar. 1988.

Smith et al., "Studies of Nucleic Acid Reassociation Kinetics: Reactivity of Single-Stranded Tails in DNA-RNA Renaturation," Proc. Natl. Acad. Sci. USA, vol. 72, pp. 4805-4809, Dec. 1975.

Lucas et al., "Rapid Human Chromosome Aberration Analysis Using Fluorescence In Situ Hybridization," Int. J. Radiat. Biol., vol. 56, pp. 35-44, Jul. 1989.

Lichter et al., "Is Non-Isotopic In Situ Hybridization Finally Coming of Age?," Nature, vol. 345, pp. 93-94, May 3, 1990.

Emmerich et al., Interphase Cytogenetics in Paraffin Embedded Sections from Human Testicular Germ Cell Tumor Xenografts and in Corresponding Cultured Cells, Lab. Invest., vol. 61, pp. 235-242, Aug. 1989.

Manuelidis et al., "Reproducible compartmentalization of Individual Chromosome Domains in Human CNS Cells Revealed by In Situ Hybridization and Three-Dimensional Reconstruction," Chromosoma, vol. 96, pp. 397-410, 1988.

Schardin et al., "Specific Staining of Human Chromosomes in Chinese Hamster × Man Hybrid Cell Lines Demonstrates Interphase Chromosome Territories," Hum. Genet., vol. 71, pp. 281-287, 1985.

Dauwerse et al., "Rapid Detection of Chromosome 16 Inversion in Acute Nonlymphocytic Leukemia, Subtype M4: Regional Localization of the Breakpoint in 16p," Cytogenet. Cell Genet., vol. 53, pp. 126-128, 1990.

Laforgia et al., "Detailed Genetic and Physical Map of the 3p Chromosome Region Surrounding the Familial Renal Cell Carcinoma Chromosome Translocation, t(3;8)(p14.2;q24.1)," Cancer Res., vol. 53, pp. 3118-3124, 1993.

Weber-Matthiesen et al., "Translocation t(2;5) is Not a Primary Event in Hodgkin's Disease," Am. J. Pathol., vol. 149, pp. 463-467, Aug. 1996.

Pinkel et al., "Cytogenetic Analysis by In Situ Hybridization with Fluorescently Labeled Nucleic Acid Probes," Cold Spring Harb. Symp. Quant. Biol., vol. 51, pp. 151-157, 1986.

Weber-Matthiesen et al., "Rapid Immunophenotypic Characterization of Chromosomally Aberrant Cells by the New FICTION Method," Cytogenet. Cell Genet., vol. 63, pp. 123-125, 1993.

Weber-Matthiesen et al., "Simultaneous Fluorescence Immunophenotyping and Interphase Cytogenetics: A Contribution to the Characterization of Tumor Cells," J. Histochem. Cytochem., vol. 40, pp. 171-175, 1992.

Nederlof et al., "Detection of Chromosome Aberrations in Interphase Tumor Nuclei by Nonradioactive In Situ Hybridization," Cancer Genet. Cytogenet., vol. 42, pp. 87-98, 1989.

Hopman et al., "Bi-color Detection of Two Target DNAs by Non-Radioactive In Situ Hybridization," Histochemistry, vol. 85, pp. 1-4, 1986.

Van Der Plas et al., "Cytogenetic and Molecular Analysis in Philadelphia Negative CML," Blood, vol. 73, pp. 1038-1044, Mar. 1989.

Rappold et al., "Sex Chromosome Positions in Human Interphase Nuclei as Studied by In Situ Hybridization with Chromosome Specific DNA Probes," Hum. Genet., vol. 67, pp. 317-325, 1984.

Cremer et al., "Detection of Chromosome Aberrations in the Human Interphase Nucleus by Visualization of Specific Target DNAs with Radioactive and Non-Radioactive In Situ Hybridization Techniques: Diagnosis of Trisomy 18 with Probe L1.84," Hum. Genet., vol. 74, pp. 346-352, 1986.

Landegent et al., "Use of Whole Cosmid Cloned Genomic Sequences for Chromosomal Localization by Non-Radioactive In Situ Hybridization," Hum. Genet., vol. 77, pp. 366-370, 1987.

Lichter et al., "Delineation of Individual Human Chromosomes in Metaphase and Interphase Cells by In Situ Suppression Hybridization Using Recombinant DNA Libraries," Hum. Genet., vol. 80, pp. 224-234, 1988.

Nederlof et al., "Three-Color Fluorescence In Situ Hybridization for the Simultaneous Detection of Multiple Nucleic Acid Sequences," Cytometry, vol. 10, pp. 20-27, 1989.

Cremer et al, "Detection of Chromosome Aberrations in Metaphase and Interphase Tumor Cells by In Situ Hybridization Using Chromosome-Specific Library Probes," Hum. Genet., vol. 80, pp. 235-246, 1988.

Landegent et al., "Chromosomal Localization of a Unique Gene by Non-Autoradiographic In Situ Hybridization," Nature, vol. 317, pp. 175-177, 1985.

Pinkel et al., "Fluorescence in situ Hybridization with Human Chromosome-Specific Libraries: Detection of Trisomy 21 and Translocations of Chromosome 4," Proc. Natl. Acad. Sci. USA, vol. 85, pp. 9138-9142, Dec. 1988.

Pinkel et al., "Cytogenetic Analysis Using Quantitative, High-Sensitivity, Fluorescence Hybridization," Proc. Natl. Acad. Sci. USA, vol. 83, pp. 2934-2938, May 1986.

Hopman et al, "A New Hybridocytochemical Method Based on Mercurated Nucleic Acid Probes and Sulfhydryl-Hapten Ligands. I. Stability of the Mercury-Sulfhydryl Bond and Influence of the Ligand Structure on Immunochemical Detection of the Hapten," Histochemistry, vol. 84, pp. 169-178, 1986.

Nagasaki et al., "An Enzyme Immunoassay for Carcinoembryonic Antigen (CEA) with Homogeneous Reactivity to Different CEA Preparations and Low Cross-Reactivity with CEA-Related Normal Antigens," J. Immunol. Meth., vol. 162, pp. 235-245, 1993.

Tkachuk et al., "Detection of bcr-abl Fusion in Chronic Myelogeneous Leukemia by In Situ Hybridization," Science, vol. 250, pp. 559-562, Oct. 26, 1990.

Tkachuk et al., "Clinical Applications of Fluorescence In Situ Hybridization," Genet. Anal. Techniq. Appl., vol. 8, pp. 67-74, 1991.

Thompson et al., "Cytogenetic Profiling Using Fluorescence In Situ Hybridization (FISH) and Comparative Genomic Hybridization (CGH)," J. Cell. Biochem., vol. 17G, pp. 139-143, 1993.

Du Manoir et al., "Detection of Complete and Partial Chromosome Gains and Losses by Comparative Genomic In Situ Hybridization," Hum. Genet., vol. 90, pp. 590-610, 1993.

Apr. 5, 2005, Non-Final Office Action Issued to U.S Appl. No. 10/739,870.

Search Report for International Application PCT/DK99/00245.

* cited by examiner

METHOD AND PROBES FOR THE DETECTION OF CHROMOSOME ABERRATIONS

This application is a continuation of U.S. application Ser. No. 09/674,792, filed Dec. 21, 2000 now abandoned, which is the U.S. National Phase of PCT/DK99/00245, filed May 4, 1999, and claiming priority to Denmark Application DK 1998 00615, filed May 4, 1998. The entire teachings of the above applications are incorporated herein by reference.

The present invention relates to a novel method for detection of chromosome aberrations. More specifically, the present invention relates to the determination of chromosome aberrations by in situ hybridisation using at least two sets of hybridisation probes, at least one set comprising one or more peptide nucleic acid probes capable of hybridising to specific nucleic acid sequences related to a potential aberration in a chromosome, and at least another set comprising one or more peptide nucleic acid probes capable of hybridising to specific nucleic acid sequences related to another or the same potential aberration in a chromosome. In particular, the present invention relates to the determination of chromosome aberrations by in situ hybridisation using at least two sets of hybridisation probes, at least one set comprising one or more peptide nucleic acid probes capable of hybridising to specific nucleic acid sequences flanking one side of a potential breakpoint in a chromosome, and at least another set comprising two or more peptide nucleic acid probes capable of hybridising to specific nucleic acid sequences flanking the other side of the potential breakpoint in the chromosome. The invention further relates to such sets of hybridisation probes.

BACKGROUND OF THE INVENTION

Chromosome aberrations are well recognised to play an important role as a cause for diseases, not least as a cause for malignant diseases. Detection of such aberration is, therefore, an important target for novel diagnostic tools. Well known techniques known in the arts of molecular biology and chromosome analyses are thus currently applied for detection of these important causes of diseases. So far, however, a fast, convenient, cheap and user-friendly test which allows for widespread and routine detection of chromosome aberrations has not been available.

According to i.a. the international patent application, publication no. WO 93/24652 (ref. 1) it has been found that peptide nucleic acids hybridise fast, selectively and strongly to nucleic acids such as, for example, chromosomes or nucleic acids derived from chromosomes.

According to the international patent application, publication no. WO 97/18325 (ref. 2) i.a. chromosome aberrations can be detected by hybridising peptide nucleic acids to chromosomes or fragments thereof followed by detection of the binding pattern of the peptide nucleic acids.

An area of particular interest regarding chromosome aberration are the so called breakpoints that have been demonstrated in numerous cases to be specifically linked to the development of malignant diseases.

SUMMARY OF THE INVENTION

In the broadest aspect, the present invention provides a method of determining the presence of chromosome aberrations in a sample of eukaryotic origin using in situ hybridisation, comprising the steps of a) producing a preparation of the sample, whereby the sample will be subject to a fixation, b) contacting said preparation with a hybridisation solution comprising at least two sets of hybridisation probes, at least one set comprising one or more peptide nucleic acid probes capable of hybridising to specific nucleic acid sequences related to a potential aberration in a chromosome, and at least one set comprising one or more peptide nucleic acid probes capable of hybridising to specific nucleic acid sequences related to another or the same potential aberration in a chromosome, and optionally a hybrid destabilising agent in an amount effective to decrease the melting temperature of hybrids formed between said nucleic acid sequences and said peptide nucleic acid probes so as to increase the ratio between specific and non-specific binding, c) removing any unbound and any non-specifically bound peptide nucleic acid probe, and d) determining the presence of peptide nucleic acid probe in the preparation.

In particular, the present invention enables the determination of chromosome aberrations in the form of breakpoints.

Thus, the present invention further provides a method of determining the presence of chromosome aberrations in a sample of eukaryotic origin using in situ hybridisation, comprising the steps of a) producing a preparation of the sample, whereby the sample will be subject to a fixation, b) contacting said preparation with a hybridisation solution comprising at least two sets of hybridisation probes one set comprising, at least one or more peptide nucleic acid probes capable of hybridising to specific nucleic acid sequences flanking one side of a potential breakpoint in a chromosome, and at least one set comprising one or more peptide nucleic acid probes capable of hybridising to specific nucleic acid sequences flanking the other side of the potential breakpoint and optionally a hybrid destabilising agent in an amount effective to decrease the melting temperature of hybrids formed between said nucleic acid sequences and said peptide nucleic acid probes so as to increase the ratio between specific and non-specific binding, c) removing any unbound and any non-specifically bound peptide nucleic acid probe, and d) determining the presence of peptide nucleic acid probe in the preparation.

In a further aspect, the present invention provides a method of determining the presence of chromosome aberrations in a sample of eukaryotic origin using in situ hybridisation, comprising the steps of a) producing a preparation of the sample, whereby the sample will be subject to a fixation, b) contacting said preparation with a hybridisation solution comprising at least two sets of hybridisation probes one set comprising, one set comprising one or more peptide nucleic acid probes capable of hybridising to specific nucleic acid sequences flanking one side of a potential breakpoint in a chromosome, and one set comprising one or more peptide nucleic acid probes capable of hybridising to specific nucleic acid sequences flanking the other side of the potential breakpoint and optionally a hybrid destabilising agent in an amount effective to decrease the melting temperature of hybrids formed between said nucleic acid sequences and said peptide nucleic acid probes so as to increase the ratio between specific and non-specific binding, c) removing any unbound and any non-specifically bound peptide nucleic acid probe, and
d) determining the presence of peptide nucleic acid probe in the preparation.

In WO 97/18325 (ref. 2), a method for determining the presence of specific nucleic acid sequences in a sample of eukaryotic origin using in situ hybridisation is disclosed. The method comprises the steps of producing a preparation of the sample to be investigated, contacting the preparation with a hybridisation solution comprising at least one peptide nucleic acid probe and a hybrid destabilising agent, removing any unbound and non-specifically bound probe, and determining the presence of bound probe. The method may i.a. be used for detection of X chromosome specific sequences or centromeric sequences. In comparison, the present invention is based on a different concept, namely the use of at least two sets of hybridisation probes capable of hybridising to sequences of at least two different regions of chromosomes related to the same potential chromosome aberration or in different potential chromosome aberrations, thereby enabling determination of chromosome aberrations.

In DE 196 10 255 (ref. 3), nucleic acid sequences are disclosed, which sequences are specific for a translocation breakpoint of a chromosome. The sequences comprise a first set of sequences complementary to a DNA sequence of a first chromosome, which first set is capable of hybridising to the first DNA sequence, and a second set of sequences complementary to a DNA sequence of a second chromosome, which second set is capable of hybridising to the second DNA sequence. Only nucleic acid probes are mentioned. The use of peptide nucleic acid probes is not mentioned, nor anticipated.

EP 727 487 (ref. 4) and EP 825 198 (ref. 5) relate to Multi-tumour Aberrant Growth (MAG) genes and genes having a sequence of any one of the strands of any one of the members of the PLAG subfamily of zinc finger protein genes or CTNNB1 genes, respectively. Various methods for detecting chromosome aberrations are also described. The concept of the methods described in these two documents is different from the concept of the present invention. The methods disclosed in EP 727 487 (ref. 4) and EP 825 198 (ref. 5), respectively, are based on a comparison between the aberrant gene and the wild-type gene, whereas the method of the present invention enables direct detection of the potential chromosome aberration or aberrations. Furthermore, the use of peptide nucleic acid probes is not disclosed, nor anticipated.

DETAILED DESCRIPTION OF THE INVENTION

As mentioned above, the present invention relates to a method for determining the presence of chromosome aberrations in a sample of eukaryotic origin using in situ hybridisation, in which method at least two sets of hybridisation probes of peptide nucleic acid probes capable of hybridising to sequences related to the potential aberration or aberrations are used.

The method is suitable for detecting sequences related to a broad range of potential aberrations, and thereby determining whether aberrations are present.

The sets of hybridisation probes may be used for determining nucleic acid sequences related to different chromosome aberrations or the same aberration.

Thus, in a particular embodiment of the present method, the potential aberration is a potential breakpoint.

Other examples of such potential aberrations are deletions, amplifications, inversions, duplications and aneuploidy.

Furthermore, the present invention relates to a method for determining the presence of chromosome aberrations in a sample of eukaryotic origin using in situ hybridisation, in which method at least two sets of hybridisation probes of peptide nucleic acid probes flanking a potential breakpoint in a chromosome are used.

Suitable peptide nucleic acid probes to be used in the present invention are such containing from 8 to 40 polymerised moieties such as from 8 to 30 polymerised moieties.

Preferably, in the case of breakpoints, the sets of hybridisation probes should be chosen so as to hybridise to said specific nucleic acid sequences flanking a potential breakpoint in a chromosome within a genomic distance of no more than 100 kb, preferably no more than 50 kb from the potential breakpoint.

The probes are suitably such comprising polymerised moieties of formula (I)

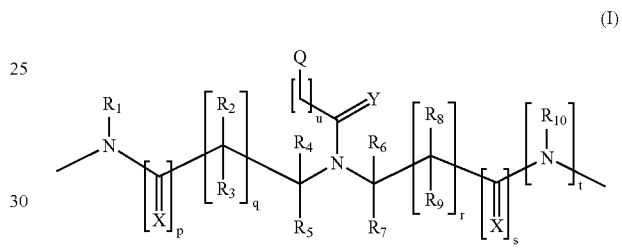

(I)

wherein
Y designates O or S,
each X independently designates O or S,
each Q independently designates a ligand that is a naturally occurring nucleobase, a non-naturally occurring nucleobase, an intercalator, a nucleobase-binding group, a label or H,
u is an integer from 0, or 1 to 5,
p and s independently designate 0 or 1,
q and r independently designate 0 or 1,
t designates 0 or 1,
$R_1$ and $R_{10}$ independently designate H or $C_{1-4}$ alkyl,
$R_2$, $R_3$, $R_4$, $R_5$, $R_6$, $R_7$, $R_8$ and $R_9$ independently designate H, the side chain of a naturally occurring amino acid, or the side chain of a non-naturally occurring amino acid.

Suitable probes are such wherein Y, X, Q, u, p, q, r, s, $R_2$, $R_5$, $R_7$ and $R_8$ are as defined above, t is 0, $R_1$ designates H or $CH_3$, and each of $R_3$, $R_4$, $R_6$ and $R_9$ designates H.

Peptide nucleic acid probes comprising polymerised moieties of formula (II), which are moieties of the general formula (I) wherein r is 0 and q and s are 1,

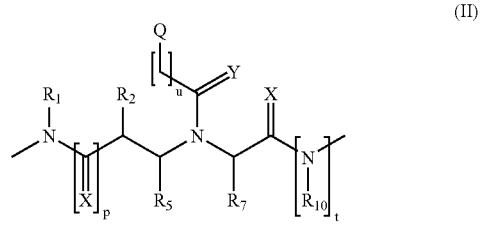

(II)

wherein Y, X, Q, p, t, u, $R_2$, $R_5$, and $R_7$ are as defined in claim 4, and $R_1$ and $R_{10}$ independently designate H or $CH_3$, are suitable for use in the present invention.

In particular, probes comprising polymerised moieties of formula (III), which are moieties of the general formula (I) wherein p, r and t are 0, and q and s are 1

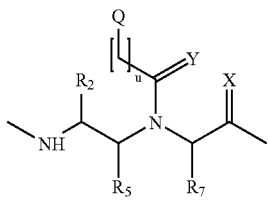

(III)

wherein Y, X, Q, u, $R_2$, $R_5$ and $R_7$ are as defined above, may be used.

In a special embodiment, peptide nucleic acid probe comprising polymerised moieties of formulas (IV), (V) and/or (VI), which are moieties of the general formula (I) wherein p, r and t are 0, and u, s and q are 1,

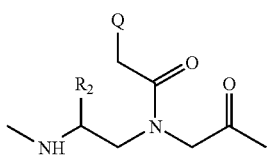

(IV)

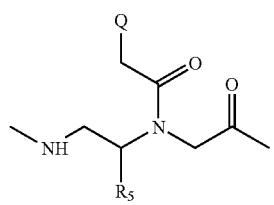

(V)

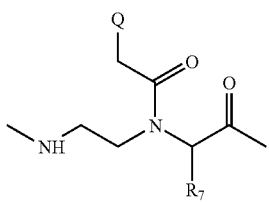

(VI)

wherein $R_2$, $R_5$, and $R_7$ are as defined above, and each Q independently designates a naturally occurring nucleobase, a non-naturally occurring nucleobase, an intercalator or a nucleobase-binding group, may be used. In particular, $R_2$, $R_5$ and $R_7$ may designate H or the side chain of Ala, Asp, Cys, Glu, His, HomoCys, Lys, Orn, Ser or Thr, and Q designates thymine, adenine, cytosine, guanine, uracil or hypoxanthine.

Preferred peptide nucleic acid probe are those comprising polymerised moieties of formula (VII), which are moieties of formula (I) wherein p, r and t are 0, and u, s and q are 1

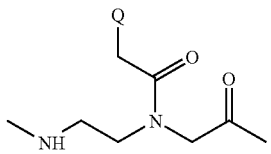

(VII)

wherein Q designates thymine, adenine, cytosine, guanine, uracil or hypoxanthine.

The method of the invention can be used for detecting a broad range of chromosome aberrations, and further can be used for the diagnosis of disorders and diseases related to chromosomal aberrations or abnormalities such as e.g. haemapoietic malignancies, cancers and inborn constituel diseases. Furthermore, the method may be used for detecting viral sequences and their localisation in the chromosome.

The term "chromosome aberration" is intended to mean translocation, amplification, inversion, duplication and aneuploidy.

The term "nucleic acid sequences related to a potential aberration in a chromosome" is intended to comprise a region and regions of a chromosome/chromosomes of interest in relation to the aberration or aberrations in question.

Examples of chromosome aberration-related disorders or diseases are acute lymphoblastic leukemias (ALL), chronic lymphotic leukemias, non-Hodgkin's lymphomas (NHL), malignant lymphomas, and multiple lymphomas. Well-established chromosome aberrations have been identified in many events. Often the particular chromosome aberration can be used to forecast the prognosis as some genetic aberrations are associated with favourable prognosis, whereas others are associated with poor prognosis.

Examples of other chromosome aberrations related to solid tumours and cancers are HER-2 (ERBB2) gene amplification frequently related to breast cancers. A breast cancer panel may also include e.g. CMYC (c-myc) amplification, EGFR (epidermal growth factor receptor) amplification or duplication, amplification of genes localised to chromosome 20q13, TP53 (p53) deletion, and RB deletion. For other cancer types similar panels may be chosen. Also, some of the aberrations mentioned occur in other cancer types.

Lymphoid malignancies are manifested in a broad range of diseases which differ in clinical symptoms, prognosis and treatment regimen. Such malignancies can be divided into B-cell malignancies and T-cell malignancies. ALL can further can further be classified as pro-B-ALL, common-ALL, pre-B-ALL and additional T-ALL types.

In the case of ALL and NHL, several different types of chromosome aberrations have been identified. For example, translocations resulting in fusion genes encoding for fusion proteins with new or modified functions have been identified in precursor-B-ALL (e.g. E2A-PBX and BCR-ABL fusion proteins from t(1;19) and t(9;22), respectively). In acute leukemias, the 11q23 region with the MLL gene is important. Other examples are t(14;18) with involvement of the BCL2 gene, t(11;14) with involvement of the BCL1/Cyclin D1 gene, TAL1 deletions in T-ALL, t(12;21) in precursor-B-ALL, and t(2;5) in anaplastic large cell lymphoma. Further examples are t(4;11) (q21;q23) involving the MLL-AF4 gene, t(11;19) (q23;p13) involving the MLL-ENL gene, t(6;11) (q27;q34) involving the MLL-AF6 gene, and t(9;11) (p22;q23) involving the MLL-AF9 gene in the case of acute leukemias, t(2;18) (p12;q21) involving the IGK-BCL2 gene, and t(18;22) (q21;q11) involving the IGL-BCL2 gene in the case of malignant lymphomas, and t(11;22)(q24;q12) involving the EWS-FLI1 gene, t(21;22)(q22;q12) involving the EWS-ERG gene, and t(7;22) (p22;q12) involving the EWS-ETV1 gene in the case of solid tumours.

In the method of the invention each peptide nucleic acid probe is suitably labelled directly or indirectly with at least one detectable label such as those selected from the group consisting of enzymes, chromophores, fluorochromes, and haptens. Furthermore, various systems for enhancing or amplifying the signal may also be applied. Such systems are well-known in the art.

In a preferred embodiment of the invention labels are attached to the peptide nucleic acids in such a fashion that all peptide nucleic acids of one set of probes is labelled with one specific label while the peptide nucleic acids of the other set are labelled with another specific label.

For example, in the case of detection of breakpoints the use of different labels is an interesting option. By monitoring the fluorescence after hybridising the two sets of probes to the nucleic acid target to be investigated the presence or absence of a breakpoint is readily apparent from the combined fluorescence of the peptide nucleic acid probe sets: if the two fluorescent signals are fused no break has occurred while the presence of two separate signals from each set of peptide nucleic acid probes indicates, that a break has occurred between the target regions or targets investigated.

The method of the invention can be carried out using various forms of detectable labels and detection methods. Also, the method of the invention may be utilised for simultaneous detection of several aberrations by employing several sets of peptide nucleic acid probes.

Peptide nucleic acids to be used according to the method of the invention can be selected on the basis of sequence analysis of nucleic acid regions to be investigated. The peptide nucleic acids can be synthesised and labelled according to methods known in the art.

Hybridisation of the peptide nucleic acid sets to target material under investigation can be carried out for example as exemplified in the international patent application no. WO 97/18325 (ref. 2). Subsequent detection of the peptide nucleic acid hybridisation pattern is carried out according to methods well known in the art.

The hybrid destabilising agent is present in an amount effective to decrease the melting temperature of hybrids formed between the nucleic acid to be determined and the peptide nucleic acid probe used to detect said nucleic acid so as to increase the ratio between specific binding and non-specific binding. Within the present context, specific binding is intended to mean that the occurrence of false positive signals due to binding of the probes to other nucleic acid sequences having the same or similar sequence as the target sequence is reduced sufficiently to ensure determination under the used conditions.

Examples of hybrid destabilising agents are formamide, urea, ethylene glycol, guanidine and glycerol. Most of these agents may preferably be present in an amount of above 10% and less than 80%, such as 70%. Formamide and guanidine may more preferably be present in an amount of from 20% to 80%, more preferably of from 20% to 60%, most preferably of from 30% to 70% or from 30% to 50%. Urea is preferably used in a concentration from 2 to 5 M. Ethylene glycol may more preferably be present in an amount of from 30% to 65%, most preferably of from 50% to 65%.

The present invention provides a method for determining the presence of specific nucleic acid sequences in samples of eukaryotic origin, such as of human, animal or plant origin. Non-limiting examples are tissue sections, cell smears, suspensions of cells or parts thereof and chromosome spreads. The presence of viral and/or bacterial DNA as well as non-eukaryotic DNA incorporated into eukaryotic DNA also may be detected using the present method.

The peptide nucleic acid probe may suitably be labelled or unlabelled. In one aspect, the peptide nucleic acid probe carries one or more labels for detection of hybrids formed during hybridisation.

In one embodiment of the present invention, a washing buffer at alkaline pH may preferably be used in step (c). The use of a washing buffer having an alkaline pH may in some cases provide an increased ratio between specific binding and non-specific binding.

In another aspect, the present invention concerns a pair of set of hybridisation probes, one set hybridising to specific nucleic acid sequences related to a potential aberration of a chromosome, and one set hybridising to specific nucleic acid sequences related to another or the same potential aberrations of a chromosome, each set comprising one or more peptide nucleic acid probes of formula (I) to (VII). In one embodiment, the pair of sets is such, wherein the sets are capable of hybridising to nucleic acid sequences related to different chromosome aberrations. In another embodiment, the pair of sets is such which comprises sets of hybridisation probes capable of hybridising to different nucleic acid sequences related to the same potential aberration. An example of the latter is sets of probes capable of hybridising to nucleic acid sequences related to a potential breakpoint.

The invention further relates to a pair of sets of hybridisation probes, one set hybridising to specific nucleic acid sequences flanking one side of a potential breakpoint in a chromosome and another set hybridising to specific nucleic acid sequences flanking the other side of the potential breakpoint and each set comprising one or more peptide nucleic acid probes of formula (I) to (VII). The pair of sets of hybridisation probes is preferably such wherein each set hybridises to specific nucleic acid sequences flanking either side of a potential breakpoint in a chromosome within a genomic distance of no more than 100 kb, preferably no more than 50 kb from the potential breakpoint.

The pair of sets of hybridisation probes according to the invention is preferably such in which each set comprises from 1 to 500, from 1 to 250, from 1 to 100, from 1 to 35 peptide nucleic acid probes.

The invention also relates to an in situ diagnostic method for diagnosing chromosome aberrations in a sample of eukaryotic origin comprising the steps of a) producing a preparation of the sample, whereby the sample will be subject to a fixation, b) contacting said preparation with a hybridisation solution comprising at least two sets of hybridisation probes, at least one set comprising one or more peptide nucleic acid probes capable of hybridising to specific nucleic acid sequences related to a potential aberration in a chromosome, and at least another set comprising one or more peptide nucleic acid probes capable of hybridising to specific nucleic acid sequences related to another or the same potential aberration in a chromosome, and optionally a hybrid destabilising agent in an amount effective to decrease the melting temperature of hybrids formed between said nucleic acid sequences and said peptide nucleic acid probes so as to increase the ratio between specific and non-specific binding, c) removing any unbound and any non-specifically bound peptide nucleic acid probe, and d) determining the presence of peptide nucleic acid probe in the preparation.

In particular, one embodiment of the diagnostic method is an in situ diagnostic method for diagnosing chromosome aberrations in a sample of eukaryotic origin comprising the steps of
a) producing a preparation of the sample, whereby the sample will be subject to a fixation,
b) contacting said preparation with a hybridisation solution comprising at least two sets of hybridisation probes, at least one set comprising one or more peptide nucleic acid probes capable of hybridising to specific nucleic acid sequences flanking one side of a potential breakpoint in a chromosome, and at least one set comprising one or more peptide nucleic acid probes capable of hybridising to specific nucleic acid sequences flanking the other side of the potential breakpoint and optionally a hybrid destabilising agent in an amount effective to decrease the melting temperature of hybrids formed between said nucleic acid sequences and said peptide nucleic acid probes so as to increase the ratio between specific and non-specific binding,
c) removing any unbound and any non-specifically bound peptide nucleic acid probe, and
d) determining the presence of peptide nucleic acid probe in the preparation.

In a further embodiment of the diagnostic method, the method concerns an in situ diagnostic method for diagnosing chromosome aberrations ill a sample of eukaryotic origin comprising the steps of
a) producing a preparation of the sample, whereby the sample will be subject to a fixation,
b) contacting said preparation with a hybridisation solution comprising at least two sets of hybridisation probes, one set comprising one or more peptide nucleic acid probes capable of hybridising to specific nucleic acid sequences flanking one side of a potential breakpoint in a chromosome, and one set comprising one or more peptide nucleic acid probes capable of hybridising to specific nucleic acid sequences flanking the other side of the potential breakpoint and optionally a hybrid destabilising agent in an amount effective to decrease the melting temperature of hybrids formed between said nucleic acid sequences and said peptide nucleic acid probes so as to increase the ratio between specific and non-specific binding,
c) removing any unbound and any non-specifically bound peptide nucleic acid probe, and
d) determining the presence of peptide nucleic acid probe in the preparation.

The invention further concerns the use of a pair of sets of hybridisation probes as defined above for use in the method of the invention, and for use in the in vitro diagnostic method of the invention.

Starting Material

The present method can be used to detect nucleic acid sequences in samples of eucaryotic origin. It is contemplated that the present method provides a valuable tool for analysing such samples for the presence of nucleic acid sequences specific for e.g. pathogenic bacteria or virus hence providing information for establishing a diagnosis. In human or animal pathology, the detection of chromosomal aberrations may provide clinically important information for diagnosing genetic disorders or diseases. In plant biology, it is further contemplated that the present method may be a valuable tool for monitoring the efficiency of transferring for example herbicide resistance genes to a plant or, like in human tissues, to establish specific synthesis of proteins (by detection of mRNA) in a given cell structure.

The term "sample of eukaryotic origin" includes, but is not limited to samples of human, animal or plant origin. In the present context, the term "sample" is intended to include, but is not limited to, human, animal or plant tissue sections, cell or tissue cultures, suspension of human, animal or plant cells or isolated parts thereof, human or animal biopsies, blood samples, saliva, urine, cerebrospinal fluid, milk, excretions, secretions, swabs, faecal samples and aspirates.

Producing a Preparation of the Sample

The sample to be examined is pre-treated before the hybridisation step whereby a preparation of the sample is produced. The person skilled in the art will readily recognise that the appropriate pre-treatment will depend on the type of sample to be examined. During the pre-treatment, the sample will be subject to a fixation.

Thus, in one embodiment of the method, the sample is deposited onto a solid support. Techniques for depositing a sample onto the solid support will depend upon the type of sample in question and may include, for example, sectioning of tissue as well as smearing or cytocentrifugation of cell suspensions. Many types of solid supports may be utilised to practice the present method. The use of such supports and the procedures for depositing samples thereon are known to those skilled in the art. Glass microscope slides are especially convenient. Glass microscope slides can be treated to better retain the sample.

Prior to hybridisation, the sample is suitably pre-treated with various chemicals and/or enzymes to facilitate the subsequent reactions. The actual pre-treatment will depend on the type of sample to be analysed. The preferred treatment is one which fixes and preserves the morphological integrity of the cellular matrix and of the nucleic acids within the cell as well as enables the most efficient degree of probe penetration.

In producing a preparation of a tissue sample, the morphological integrity of a tissue and the integrity of the nucleic acids can be preserved by bringing the sample to a fixed stage either by means of chemical fixation or freezing. When freezing is used for preservation of for instance a biopsy, the biopsy is typically frozen in liquid nitrogen. After freezing, the sample may appropriately be stored at −80° C. Prior to the analysis of the nucleic acid, the frozen sample is cut into thin sections and transferred to e.g. pre-treated slides. This can e.g. be carried out at a temperature of −20° C. in a cryostat. The biopsy or tissue sections may suitably be stored at −80° C. until use. Prior to hybridisation, the tissue section may be treated with a fixative, e.g. a precipitating fixative such as acetone and/or the tissue section is incubated for a short period in a solution of buffered formaldehyde. Alternatively, the biopsy or tissue section can be transferred to a fixative such as buffered formaldehyde for 12 to 24 hours. Following fixation, the tissue may be embedded in paraffin forming a block from which thin sections can be cut. Well prepared paraffin-embedded samples can be stored at room temperature for a period of years.

Prior to hybridisation, the tissue section is deparaffinated and re-hydrated using standard procedures.

Further permeabilisation may be necessary in order to ensure sufficient accessibility of the target nucleic acid sequences to the peptide nucleic acid probe. The type of treatment will depend on several factors, for instance on the fixative used, the extent of fixation, the type and size of sample used and the length of the peptide nucleic acid probe.

The treatment may involve exposure to protease such as proteinase K, pronase or pepsin, diluted acids, detergents or alcohols or a heat treatment.

In some cases, a pre-hybridisation step using a pre-hybridisation mixture very similar to the hybridisation solution but without the peptide nucleic acid probe or another pre-hybridisation, solution without probe, might be useful in order to decrease non-specific binding of the peptide nucleic acid probe. The components of the pre-hybridisation mixture should be selected so as to obtain an effective saturation of sites in the tissue that might otherwise bind the peptide nucleic acid probe non-specifically.

For analysing a suspended preparation such as a suspension of cells, the sample is treated so as to obtain a permeabilisation of the material and a preservation of the morphology. Fixation may be carried out with a fixative such as formaldehyde, acetone or ethanol.

The present method permits the detection of a specific nucleic acid sequence in a chromosome. Such detection may for example be carried out using spreads of chromosomes in metaphase, where the target sequence may be located in any region of the chromosomes. A sample preparation may in this case comprise adding an agent such as colcemide to arrest the chromosomes of dividing cells in the metaphase of the mitosis. Subsequently, the sample may be treated with a hypotonic buffer. Following centrifugation, the chromosomes are treated with a fixative and spread on a slide. Immediately before or simultaneously with the hybridisation step, the preparation may be treated to separate the double-stranded target. This separation can be achieved by heating the preparation in the presence of a denaturing agent such as formamide. The detection of a specific nucleic acid sequence in a chromosome may also be carried out using chromosomes in interphase, e.g. in tissue sections or in a suspension of cells. In such cases, the specimens may be treated as described above for tissue sections or suspension of cells.

For all sample preparations, the nucleic acids are fixed in a morphological structure allowing hybridisation to be carried out in situ. Thus, the nucleic acids are not extracted from the cellular material and the hybridisation is not carried out in solution.

Peptide Nucleic Acids to be Used in the Present Method

The term "naturally occurring nucleobases" includes the four main DNA bases (i.e. thymine (T), cytosine (C), adenine (A) and guanine (G)) as well as other naturally occurring nucleobases (e.g. uracil (U) and hypoxanthine).

The term "non-naturally occurring nucleobases" comprises, e.g., naturally occurring nucleobases wherein a label is coupled to the base optionally through a suitable linker, and modified naturally occurring nucleobases such as, e.g., modified uracil and hypoxanthine. Other examples of non-naturally occurring nucleobases are 2,6-diamino purine, propynylcytosine (C propynyl), isocytosine (iso-C), isopseudocytosine (iso$^{pseudo}$C), 5-methyl-isocytosine (iso$^{Ile}$C), and thiouracil (see e.g. Tetrahedron Letters Vol 36, No 21, 3601–3604 (1995) (ref. 6)).

Examples of useful intercalators are e.g. acridin, antraquinone, psoralen and pyrene.

Examples of useful nucleobase-binding groups are e.g. 3-nitro pyrrole and 5-nitro indole.

In the present context, "$C_{1-4}$ alkyl" is intended to mean branched or non-branched alkyl groups containing 1 to 4 carbon atoms. Non-limiting examples are $CH_3$, $CH_2CH_3$ and $CH(CH_3)_2$.

Within the present context, the expression "naturally occurring amino acid" is intended to comprise D- and L-forms of amino acids commonly found in nature, e.g. D- and L-forms of Ala (alanine), Arg (arginine), Asn (aspargine), Asp (aspartic acid), Cys (cysteine), Gln (glutamine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine) and Val (valine).

In the present context, the expression "non-naturally occurring amino acid" is intended to comprise D- and L-forms of amino acids other than those commonly found in nature as well as modified naturally occurring amino acids. Examples of useful non-naturally occurring amino acids are D- and L-forms of Cha (cyclohexylalanine), Cit (citrulline), Hci (homocitrulline), HomoCys (homocystein), Hse (homoserine), Nle (norleucine), Nva (norvaline), Orn (ornithine), Sar (sarcosine) and Thi (thienylalanine).

The peptide nucleic acid probes to be used in the present method should comprise a sufficient number of ligands capable of interacting with the nucleotide sequence to be determined to form hybrids sufficiently stable under the stringency used in the hybridisation and in the post-hybridisation wash. The strategy for selecting the ligands of the peptide nucleic acid probe to be used in accordance with the present method may be based on available target nucleotide sequence information.

In the above-indicated peptide nucleic acid probes, the backbone of the moieties may preferably consist of six atoms. This has been shown to provide the presently strongest observed affinity for nucleic acids. It may in some cases be advantageous to change the strength of the binding between the peptide nucleic acid probe and the nucleic acid sequence. Such change of the affinity may be accomplished by separating the ligands by fewer or by more atoms than six atoms. It is contemplated that preferred peptide nucleic acid probes to be used in the present method comprise less than 25% by weight (calculated excluding X and Q groups as well as any linkers and/or labels) of moieties having more or less than six atoms in the backbone.

The strength of the binding between the peptide nucleic acid probe and the nucleic acid sequence is influenced by the ligand Q. Hoogsteen and/or Watson-Crick base pairing assist in the formation of hybrids between a nucleic acid and a peptide nucleic acid probe wherein Q designates a nucleobase. It is contemplated that one or more of the ligands may be a group which contribute little or none to the binding of the nucleic acid such as hydrogen. It is contemplated that peptide nucleic acid probes to be used in the present method comprise less than 25% by weight moieties wherein Q designate H. One or more of the ligands Q may be groups that stabilise nucleobase stacking such as intercalators.

In the above-indicated peptide nucleic acid probes, one or more of the Q-groups may designate a label. Examples of suitable labels are given below. Moieties wherein Q denotes a label may preferably be located in one or both of the terminating moieties of the peptide nucleic acid. Moieties wherein Q denotes a label may also be located internally.

The peptide nucleic acid comprises polymerised moieties as defined above. From the formula, it is to be understood that the peptide nucleic acid probe may comprise polymerised moieties the structure of which may be mutually different or identical.

The backbone of the peptide nucleic acid probe may suitably form a polyamide comprising polymerised moieties, wherein all X groups are O, or form a polythioamide comprising polymerised moieties, wherein all X groups are S. The polyamide and polythioamide forming moieties may be linked to form probes comprising both polyamide and polythioamide forming moieties or to form probes comprising polyamide forming moieties or polythioamide forming moieties only. Peptide nucleic acid probes having a polyamide backbone (all X groups designate O) are of particular interest.

The preferred length of the peptide nucleic acid probe will depend on the target material and whether labelled peptide nucleic acid probes are used. It is contemplated that especially interesting peptide nucleic acid probes comprise from 8 to 40 polymerised moieties as defined above. Peptide nucleic acid probes comprising from 8 to 30, from 12 to 25, or from 12 to 20 polymerised moieties may be of particular interest, and peptide nucleic acid probes comprising from 14 to 23, and from 14 to 20 moieties are of most interest.

As mentioned above, the polymerised moieties of the peptide nucleic acid probe may be mutually different or identical. In some embodiments, the polymerised moieties of formulas (IV)–(VII) constitute at least 75% by weight (calculated as defined above), preferably at least 80% by weight and most preferably at least 90% by weight of the probe.

The ends on the moieties terminating the peptide nucleic acid may be substituted by suitable substituents. The substituents may be chosen so as to form the free or acylated form of the terminating moiety. The substituents may further be chosen so as to form an ester, an amide or an amine depending on the chemical nature of the terminating moiety. A terminating end may further be substituted by one or more labels, which labels may be incorporated end to end, i.e. so as to form a non-branched labelled end, or may be incorporated so as to form a branched labelled end ("zipper"). A terminating end may further be substituted by one or more linker units. Such linker units may be attached directly to a terminating end, may be attached to a label or between labels on a terminating end, or be attached to a terminating end before a label is attached to a terminating end. It should be understood that two terminating ends may carry different or identical substituents, linker units and/or labels. It should further be understood that the term "a label" is intended to comprise one or more labels.

The expression "peptide label" is intended to mean a label comprising from 1 to 20 naturally occurring or non-naturally occurring amino acids, preferably from 1 to 10 naturally occurring or non-naturally occurring amino acids, more preferably from 1 to 8 naturally occurring or non-naturally occurring amino acids, most preferably from 1 to 4 naturally occurring or non-naturally occurring amino acids, linked together end to end in a non-branched or branched ("zipper") fashion. In a preferred embodiment, such a non-branched or branched end comprises one or more, preferably from 1 to 8 labels, more preferably from 1 to 4, further labels other than a peptide label. Such further labels may suitably terminate a non-branched end or a branched end. One or more linker units may suitably be attached to the terminating end before a peptide label and/or a further label is attached. Such linker units may also be attached between a peptide label and a further label.

The probe as such may also comprise one or more labels such as from 1 to 8 labels, preferably from 1 to 4 labels, and/or one or more linker units, which may be attached internally, i.e. to the backbone of the probe. The linker units and labels may mutually be attached as described above.

In the present context, the term "label" refers to a substituent which is useful for detection of hybrids formed between a peptide nucleic acid probe and a nucleic acid. In accordance with the present invention, suitable labels comprise fluorophores, biotin, dinitro benzoic acid, digoxigenin, radioisotope labels, peptide or enzyme labels, dyes, chemiluminiscence labels, hapten, antigen or antibody labels, and spin labels. Examples of particular interesting labels are biotin, fluorescent labels, such as fluorescein labels, e.g. 5-(and 6)-carboxyfluorescein, 5- or 6-carboxyfluorescein, 6-(fluorescein)-5-(and 6)-carboxamido hexanoic acid and fluorescein isothiocyanate, peptide labels, dinitro benzoic acid, rhodamine, tetramethylrhodamine, cyanine dyes such as Cy2, Cy3 and Cy5, optionally substituted coumarin, R-phycoerythrin, allophycoerythrin, Texas Red and Priricesston Red as well as conjugates of R-phycoerythrin and, e.g. Cy5 or Texas Red.

Examples of preferred labels are biotin, fluorescent labels, peptide labels and dinitro benzoic acid. Peptide labels may preferably be composed of from 1 to 10, more preferably of from 1 to 8, most preferably of from 1 to 4, naturally occurring or non-naturally occurring amino acids. It may be particularly advantageous to incorporate one or more other labels as well as a peptide label such as from 1 to 8 or from 1 to 4 other labels. Two of such other labels may e.g. be incorporated at each terminating end.

Suitable peptide labels may preferably be composed of cysteine, glycine, lysine, ornithine, glutamic acid or aspartic acid.

A linker may be made up of linker units selected from units of formulas —NH(CH$_2$CH$_2$O)$_n$CH$_2$C(O)—, —NH(CHOH)$_n$C(O)—, —(O)C(CH$_2$OCH$_2$)$_n$C(O)— and —NH(CH$_2$)$_n$C(O)—, wherein n is 0 or an integer from 1 to 8, preferably from 1 to 3. A linker unit may have a free amino group or a free acid group, i.e. NH$_2$(CH$_2$CH$_2$O)$_n$CH$_2$C(O)—, NH$_2$(CHOH)$_n$C(O)—, HO(O)C(CH$_2$OCH$_2$)$_n$C(O)—, NH$_2$(CH$_2$)$_n$C(O)—, —NH(CH$_2$CH$_2$O)$_n$—CH$_2$C(O)OH, —NH(CHOH)$_n$C(O)OH, —(O)C(CH$_2$OCH$_2$)$_n$C(O)OH and —NH(CH$_2$)$_n$C(O)OH. A linker may consist of up to 3 of such linker units. Examples of very interesting linker units are —NHCH$_2$C(O)—, —NHCH$_2$CH$_2$C(O)—, —NH(CH$_2$CH$_2$O)$_2$CH$_2$C(O)—, HO(O)CCH$_2$C(O)(NH(CH$_2$CH$_2$O)$_2$CH$_2$C(O))$_2$—.

In a further embodiment, the ligand Q as defined above may be labelled. Suitable labels are as defined above. Between such a label, a linker selected from C$_{1-5}$ alkyl, C$_{1-15}$ alkenyl and C$_{1-15}$ alkynyl may be incorporated. In the present context, "C$_{1-15}$ alkyl, C$_{1-15}$ alkenyl and C$_{1-15}$ alkynyl" are intended to mean branched or non-branched alkyl, alkenyl and alkynyl groups containing from 1 to 15 carbon atoms. It is preferred that such labelled ligands Q are selected from thymine and uracil labelled in the 5 position.

In a preferred embodiment, probes used are peptide nucleic acid probes comprising polymerised N-(2-aminoethyl) glycine moieties of formula (VII) wherein the glycine nitrogen is connected to naturally occurring nucleobases by a methylene carbonyl linker. The peptide nucleic acid probes to be used as detection probes may suitably comprise from 8 to 40, from 8 to 30 of such polymerised moieties, preferably from 12 to 25 or 12 to 20 moieties, most preferably from 14 to 23 or from 14 to 20 moieties.

Nucleobase Sequence of the Peptide Nucleic Acid Probes

The nucleobase sequence of the peptide nucleic acid probes can be obtained by analysing the nucleobase sequence of the target sequence.

The nucleobase sequence of interesting genes can e.g. be obtained from the GenBank Database, or the information can be obtained by sequencing interesting genes.

The nucleobase sequence of each set of hybridisation probes is selected having regard to the following: minimal degree of hairpin formation should be possible, minimal degree of self dimer formation should occur, and minimal degree of pair dimer formation should occur. Prospected probe sequences are compared with sequences obtained from relevant data bases like the ones available via NCBI on the world wide web.

Preparation of Peptide Nucleic Acid Probes for Hybridisation

The peptide nucleic acid probes used in the examples were synthesised according to the procedures described in "PNA Information Package" obtained from Millipore Corporation (Bedford, Mass., USA).

If using the Fmoc strategy for elongation of the peptide nucleic acid probe with linkers or amino acids, it was possible to have side chain amino groups protected with acid sensitive protection groups such as the Boc, the Mmt or the Mtt group.

One way of labelling the peptide nucleic acid probe is to use a fluorescent label, such as 5-(and 6)-carboxy-fluorescein, 5- or 6-carboxyfluorescein, 6-(fluorescein)-5-(and 6)-carboxamido hexanoic acid or fluorescein isothiocyanate. The acid group is activated with HATU (O-(7-azabenzotriazol-1-yl)-1,1,3,3-tetramethyluronium hexafluorophosphate) or HBTU (2-(1H-benzotriazol-1-yl)-1,1,3,3-tetramethyluronium hexafluorophosphate) and reacted with the N-terminal amino group or other side-chain or linker amino group. The same technique can be applied to other labelling groups containing an acid function. Alternatively, the succinimidyl ester of the above-mentioned labels may be used directly.

After synthesis, the peptide nucleic acid probes are cleaved from the resin using standard procedures as described by Millipore Corporation or PerSeptive Biosystems. The peptide nucleic acid probes can be purified and analysed using reversed-phase HPLC techniques at 50° C. and were characterised by matrix-assisted laser desorption/ionisation time of flight mass spectrometry (MALDI-TOFMS), plasma desorption mass spectrometry (PDMS) or electron spray mass spectrometry (ESMS).

Generally, peptide nucleic acid probes such as peptide nucleic acid probes comprising polyinerised moieties of formula (IV)–(VII) may also be prepared as described in, e.g., Tetrahedron Letters Vol 35, No 29, 5173–5176 (1994) (ref. 7) Chemical properties of some peptide nucleic acid probes are described in, e.g., Nature, 365, 566–568 (1993) (ref. 8)

Hybridisation

The hybridisation can be performed using fixed, immobilised or suspended preparations which are prepared as described above. If double-stranded target such as chromosomal or other DNA sequences are to be detected, a treatment to separate the two strands may be necessary. This separation of the strands can be achieved by heating the sample in the presence of the hybridisation mixture to a temperature sufficiently high and for a time period sufficiently long to dissociate the strands. Typically, heating at a temperature of 70° C. to 100° C. for a period of 1 to 15 minutes is suitable.

The hybridisation buffer may optionally comprise a hybrid destabilising agent in an amount effective to decrease the melting temperature of hybrids formed between the nucleic acid to be determined and the peptide nucleic acid probe so as to increase the ratio between specific binding and non-specific binding. This agent will allow the hybridisation to take place at a lower temperature than without the agent. In traditional nucleic acid hybridisation, such agent is called a denaturing agent.

The effective amount of the hybrid destabilising agent will depend on the type of destabilising agent used and furthermore on the peptide nucleic acid probe or combination of peptide nucleic acid probes used. It has been found that using peptide nucleic acid probes of formula (VII), particular good results have been obtained by including a hybrid destabilising agent. Examples of hybrid destabilising agents are formamide, urea, guanidine, ethylene glycol and glycerol, and most of these agents may preferably be used in a concentration above 10% and less than 80%, such as 70%. Formamide and guanidine may more preferably be present in an amount of from 20% to 80%, more preferably of from 20% to 60%, most preferably of from 30% to 70% or from 30% to 50%. Urea is preferably used in a concentration of from 2 to 5 M. Ethylene glycol may more preferably be present in an amount of from 30% to 65%, most preferably of from 50% to 65%.

It is often advantageous to include macromolecules or polymers such as dextran sulphate, polyvinylpyrrolidone and/or ficoll. In the presence of such macromolecules or polymers, the effective concentration of the peptide nucleic acid probe at the target is assumed to be increased. Dextran sulphate may be added in a concentration of up to 15%. Concentrations of dextran sulphate of from 2.5% to 12.5% are often advantageous.

In some cases, it may be advantageous to add a detergent such as sodium dodecyl sulphate, Tween 20® or Triton X-100®.

During hybridisation, other important parameters are hybridisation temperature, concentration of the peptide nucleic acid probe and hybridisation time. The person skilled in the art will readily recognise that optimal conditions for various starting materials will have to be determined for each of the above-mentioned parameters.

The hybridisation between peptide nucleic acid probes and a target nucleic acid sequence appears to be less sensitive than DNA probes to variations in pH and in the concentration of NaCl.

Post-hybridisation Washing

Following hybridisation, the preparation is washed to remove any unbound and any non-specifically bound peptide nucleic acid probes. The conditions described below are merely by way of example and may depend on the type of preparation to be analysed. During the post-hybridisation step, appropriate stringency conditions should be used in order to remove any non-specifically bound peptide nucleic acid probe. Stringency refers to the degree to which reaction conditions favour the dissociation of the formed hybrids and may be enhanced, for instance by increasing the washing temperature and washing time. For conventional hybridisation with nucleic acid probes, the salt concentration is often used as an additional factor for regulating the stringency.

Examples of useful buffer systems are Tris-Buffered-Saline (TBS), standard citrate buffer (SSC) or phosphate buffers. A convenient TBS buffer is 0.05 M Tris/HCl, 0.15 M NaCl, pH 7.6. The SSC buffer comprises 0.15 M sodium chloride and 0.015 M trisodium citrate, pH 7.0. Typically, washing buffers include a detergent such as sodium dodecylsulphate, Tween 20®, or Triton X-100®.

Typically, washing times from 5 to 30 minutes may be suitable. Washing periods of two times 10 minutes or 3 times 5 minutes in a suitable buffer may also give good results.

In some cases, particularly when using peptide nucleic acid probes carrying at least one fluorescein label, it has been shown to be advantageous to increase the pH of the washing buffer. In such cases, it is preferred that the washing solution in step (c) has a pH value of from 8 to 10.5, preferably from 9 to 10.

Detection of Hybrids Formed

In cases where the preparation is deposited onto slides, the hybridisation results may be visualised using well known immunohistochemical staining methods to detect the labelling on the peptide nucleic acid probe. When fluorescent labelled peptide nucleic acid probes are used, the hybrids may be detected using an antibody against the fluorescent label. which antibody may be conjugated with an enzyme. The fluorescent label may alternatively be detected directly using a fluorescence microscope, or the results may be automatically analysed on a fluorescent-based image analysis system.

When biotin labelled peptide nucleic acid probes are used, the hybrids may be detected using enzyme labelled streptavidin or antibodies against the biotin label which antibody may be conjugated with an enzyme. If necessary, an enhancement of the signal can be generated using commercially available amplification systems such as the catalysed signal amplification system for biotinylated probes (DAKO K 1500). Digoxigenin labelled probes may be detected using antibodies against digoxigenin, and dinitro benzoic acid with antibodies against dinitro benzoic acid.

In the case of a suspended sample such as a cell suspension, quantitative results may be obtained using peptide nucleic acid probes comprising a fluorescent label and a flow cytometer to record the intensity of fluorescence per cell. Signal amplification may be relevant for flow as well.

Peptide nucleic acid probes used in some aspects of the present method may form nucleic acid/peptide nucleic acid probe hybrids which can be recognised by an antibody described in WO 95/17430 (ref. 9). Hybrids formed between the peptide nucleic acid probe, nucleic acid and the antibody can be detected in a direct immunohistochemical staining method using, for instance an enzyme conjugated form of the antibody, followed by detection of the enzyme activity or by the application of well known indirect immunohistochemical staining techniques.

ILLUSTRATIVE EMBODIMENTS

Illustrative Embodiment 1

The method of the invention can suitably be used for detecting chromosome aberrations in ALL and NHL. The sets of hybridisation probes are chosen so as to flank each site of the potential breakpoint. Interesting regions are indicated below in Tables 1 and 2. Apart from the two sets flanking the potential breakpoint, at least one set of probes targeting fusion partner genes may be included

TABLE 1

Chromosome aberrations in ALL.

| Type of ALL | Chromosome aberration Type | Involved genes |
|---|---|---|
| Precursor-B-ALL | t(1;19) (q23;p13) | E2A-PBX1 |
| | t(4;11) (q21;q23) | MLL-AF4 |
| | t(9;22) (q34;q11) | BCR-ABL |
| | t(12;21) (p13;q22) | TEL-AML1 |

TABLE 1-continued

Chromosome aberrations in ALL.

| Type of ALL | Chromosome aberration Type | Involved genes |
|---|---|---|
| T-ALL | TAL1 deletion | SIL-TAL1 |
| | t(1;14) (q34;q11) | TAL1-TCRD |
| | t(10;14) (q24;q11) | HOX11-TCRD |
| | t(11;14) (p13;q11) | RHOM2-TCRD |

TABLE 2

Chromosome aberrations in NHL.

| Type of NHL | Chromosome aberration Type | Involved genes |
|---|---|---|
| Follicular NHL | t(14;18) | IGH-BCL2 |
| | 3q37 | BCL6 |
| Diffuse large cell centroblastic NHL | t(14;18) | IGH-BCL2 |
| | 3q27 | BCL6 |
| Large cell anaplastic NHL | t(2;5) | NPM-ALK |
| Mantle cell NHL | t(11;15) | BCL1-IGH |
| Immunoblastair NHL | t(14;18) | IGH-BCL2 |
| Burkitt's NHL | t(8;14) | MYC-IGH |
| | t(2;8) | IGK-MYC |
| | t(8;22) | IGL-MYC |
| Lymphocytic NHL | | |
| Immunocytoma | | |
| MALT-NHL | | |
| Peripheral T-NHL | | |
| Lymphoblastic T-NHL | TAL1 deletion | SIL-TAL1 |
| | t(1;14) | TAL1-TCRD |
| | t(10;14) | HOX11-TCRD |
| | t(11;14) | RHOM1-TCRD |

Illustrative Embodiment 2

Determination of Translocation Involving the Major Breakpoint (mbr) in the MLL Gene (ALL-1) and HRX The nucleobase sequences of the peptide nucleic acid probes are selected from EMBL+GenBank, Accession numbers HSALL1X28 (exon 28) and HSALL1X4 (exon 4). The nucleobases are chosen so as to form two sets of probes, a set flanking each site of the inbr region, e.g. from exon 4 and exon 28. Each set of hybridisation probes consists suitably of from 1 to 500, from 1 to 250, from 1 to 100, or from 1 to 35 peptide nucleic acid probes.

The nucleobase sequence of the probes indicated below are selected from the lower strand (i.e. they hybridise to the upper strand). The position of the nucleobases relative to the whole target sequence are indicated as "position". The first number corresponds to the position of the 5' end of the probe in the sequence, and the last number corresponds to the position of the 3' end of the probe.

Two suitable sets of probes are e.g.

| ALL-1 EXON 4 (one set) | Position | |
|---|---|---|
| GGGAAAACACAGATGGAT | 120–103 | Seq ID No 1 |
| GATTTGGTCTCTGATTTATTTAG | 145–123 | Seq ID No 2 |

-continued

| ALL-1 EXON 4 (one set) | Position | |
|---|---|---|
| GTTATTTTGATTTTTACTCCAG | 235–214 | Seq ID No 3 |
| GGTAACTCTGAAATGTCCTT | 243–262 | Seq ID No 4 |
| TTTTTCAGGCTATCTTCTT | 292–274 | Seq ID No 5 |
| CTTAAACTTAGACTTGAGAGGA | 386–365 | Seq ID No 6 |
| CCCCTTCCTTCCTATTT | 416–400 | Seq ID No 7 |
| CCTTCCTCTCCGTCGTA | 443–427 | Seq ID No 8 |
| GGGTCTTTATCCTTTCTGT | 471–453 | Seq ID No 9 |
| ACTTTCTGGGGCTTTTC | 517–501 | Seq ID No 10 |
| TGTTCCTTCCTTGTCTTTC | 539–521 | Seq ID No 11 |
| AACTGTCTTATCTTCTTTTGTA | 569–548 | Seq ID No 12 |
| CTTCGAGGGCTTTGTCT | 589–573 | Seq ID No 13 |
| GCATCTGTCCTTTTTGAA | 634–617 | Seq ID No 14 |
| CTTCTTTTTCAATTTTCTTTT | 699–679 | Seq ID No 15 |
| GGGGCACTGAATCTACTAT | 889–871 | Seq ID No 16 |
| AGCTGCACTTGATTTTTC | 923–906 | Seq ID No 17 |
| CGAATATTTTTGACCTGTG | 748–730 | Seq ID No 18 |
| GGTCATAATCCTCATCCTC | 834–816 | Seq ID No 19 |
| AGGAGATAGCACTGACAACA | 783–764 | Seq ID No 20 |
| TTTGAGAGGAGTGCTGAGA | 942–924 | Seq ID No 21 |
| TATCAACACTGGGGCTACTA | 965–984 | Seq ID No 22 |

| ALL-1 EXON 28 (another set) | Position | |
|---|---|---|
| TACTGTGACGCCTGGAG | 123–107 | Seq ID No 23 |
| AGTGGTTGGGGTAGGAC | 50–34 | Seq ID No 24 |
| GCTGGGGTGATAAGGAA | 144–128 | Seq ID No 25 |
| CGGTGGTGGAGACTGA | 225–210 | Seq ID No 26 |
| TTGAAGAGGTGGAAGTGTT | 327–309 | Seq ID No 27 |
| CACTGGACTGCTTCATTTC | 411–393 | Seq ID No 28 |
| ACTCAGCACTTTGGTCTTC | 470–452 | Seq ID No 29 |
| AAGGAGCCGATTTTACTA | 569–586 | Seq ID No 30 |
| GAGGTGTGGGAAGGAGA | 644–628 | Seq ID No 31 |
| GTTTGCTGATTGGGTAGAA | 704–686 | Seq ID No 32 |
| ATGTTCGTTGATAATGGAT | 785–767 | Seq ID No 33 |
| CTTCCTCACCAGTTGTCAC | 906–888 | Seq ID No 34 |
| CAAAACCTCATCCATAAAC | 941–923 | Seq ID No 35 |
| GACTCCTGGCATAGAAAG | 1025–1008 | Seq ID No 36 |
| TTCCGTGGTGCCTGTA | 1084–1069 | Seq ID No 37 |
| CCATTTTTAGAGGTGTCAG | 1122–1104 | Seq ID No 38 |
| CATTTTTGGATTGACTCTC | 1146–1128 | Seq ID No 39 |
| GCAGGACTACTTTCTTTCA | 1168–1150 | Seq ID No 40 |
| CTGTGGGAGATGTTGACT | 1203–1186 | Seq ID No 41 |
| TATTATTGGGGCTTGGTT | 1266–1249 | Seq ID No 42 |

The probes can of course be selected from the upper strand (i.e. so as to be capable to hybridise to the lower strand).

The probes are preferably labelled. E.g. the set of probes for exon 4 may be labelled with one or more fluorescein labels, and the set of probes for exon 28 with one or more Cy3.

Step (a): Preparation of Sample and Pre-treatment

Metaphase chromosome spreads can be prepared from peripheral blood, bone marrow, amnion, chorion villus samples or tumour cells. If prepared from peripheral blood, a sample of whole blood collected in a glass tube containing heparin or another anticoagulant is mixed with suitable growth medium. As an Example, 0,5 ml whole blood may be added to 10 ml RPMI 1640 medium supplemented with 20% (v/v) foetal calf serum, 2 mM glutamine, 100 U penicillin/streptomycin, 1% phytohemagglutinin and 5 U/ml heparin. The sample is incubated in a $CO_2$ incubator, e.g. at 37° C. for 72 h. The chromosomes are arrested in the metaphase of the mitosis, e.g. by adding colcemid (0.1 µg/ml) to the culture approximately 1½ hours before harvesting the cells.

The cells are collected by centrifugation and resuspended in a hypotonic buffer, e.g. 60 mM KCl at room temperature for about 30 minutes. The sample is treated with a suitable fixative such as methanol:acetic acid 3:1. The treatment with fixative may be repeated several times. After treatment the suspensions are left at freezing temperatures such as at −20° C. from 20 minutes to 3 days. Chromosome spreads are prepared by spotting a suitable amount of the suspension onto a clean slide and air-drying the slide.

Prior to hybridisation it may be advantageous to submit the specimens on the slides to a pre-treatment including RNAse treatment and/or additional fixation and/or protease digestion. The following procedure may e.g. be applied:
1) Immerse slides in TBS 2 min.
2) Immerse slides in 3,7% formaldehyde in TBS for 2 min.
3) Wash slides 3×5 min. in TBS.
4) Immerse slides in proper dilution of Proteinase K for 10 min at room temperature.
5) Incubate slides in RNAse 10–100 µg/ml in 2×SSC for 20–60 min. at 37° C.
6) Wash 3×5 min. in TBS.
7) Dehydrate specimens in cold ethanol series (70%, 85% and 96%) and air dry them.

Step (b): Hybridisation

Prior to hybridisation, the chromosomal DNA is denatured. Such denaturing may be carried out by placing the slide in a solution of 2×SSC and 70% formamide at about 80° C. for a short period of time such as 3–5 minutes.

Denaturation may be performed by adding the probes in proper dilution in the hybridisation buffer onto the slide containing the sample and covering it with a coverslip. The slides are then placed in a preheated incubator adjusted to 80° C. for 3 min. Hybridisation may be performed by placing the slide in the dark at room temperature or higher temperatures (50–60° C. may be suitable) for 5–60 min. A suitable hybridisation buffer is 10 mM Tris pH 7.2 with 70% formamide containing conventional blocking reagent.

Step (c): Removal of Any Unbound and Any Non-specifically Bound Peptide Nucleic Acid Probe The slide may be rinsed in TBS, pH 7.4 or 0,1×SSC to remove the coverslips followed by wash for about 5–45 min. in an appropriate washing buffer e.g. 0.1×SSC (15 mM NaCl, 1.5 mM sodium citrate pH 7.0) with 0.1% Triton X-100® or PBS with 0.1% Tween-20®.

Step (d): Detection of Hybrids Formed

If the bound probes are fluorescence labelled visible signals may be found by inspection of the slides in the fluorescence microscope at this step. Additional amplification of the signal may be provided using some of the many different immunohistochemical/immunocytochemical amplification systems well known in the art. Non-fluorescent labelled probes may also be detected using some of the many different immunohistochemical/-immunocytochemical amplification systems well known in the art.

Following appropriate amplification/detection, slides are mounted for inspection in the fluorescence microscope. A mounting media may include counter stain such as DAPI. A successful hybridisation should preferably result in easily visible signals/spots on the chromosomes and within the interfase nuclei. There should preferably be no interfering non-specific hybridisation on the chromosomes. The microscope should be correctly equipped for the labels used.

EXAMPLES

Example 1

Sequence of Peptide Nucleic Acid Probes

One set of probes targeting HER-2 was selected (Accession number emb|X03363|HSERB2R Human c-erb-B-2 mRNA). The probes were selected and numbered as described in Illustrative embodiment 2. The nucleobase sequences of the peptide nucleic acid probes were as follows:

|  | Position |  |
| --- | --- | --- |
| CAAGAGGGCGAGGAGGAG | 222–205 | Seq ID No 43 |
| GGTAGAGGTGGCGGAGCAT | 325–307 | Seq ID No 44 |
| TGGGCAGGTAGGTGAGTTC | 373–355 | Seq ID No 45 |
| GTGGGCAGGTAGGTGAGTT | 374–356 | Seq ID No 46 |
| GGCCAGGGCATAGTTGTC | 519–502 | Seq ID No 47 |
| GTATTGTTCAGCGGGTCTC | 551–533 | Seq ID No 48 |
| GCAGAGCTGGGGGTTCC | 660–644 | Seq ID No 49 |
| GAGCCAGCTGGTTGTTCT | 715–698 | Seq ID No 50 |

-continued

|  | Position |  |
| --- | --- | --- |
| GCGGTTGGTGTCTATCAGT | 738–720 | Seq ID No 51 |
| AGGCCAGGCAGTCAGAGTG | 937–919 | Seq ID No 52 |
| CCACGTCCGTAGAAAGGTA | 1099–1081 | Seq ID No 53 |
| GCAGGGGCAGACGAG | 1126–1111 | Seq ID No 54 |
| GGGCTTGCTGCACTTCTCA | 1185–1167 | Seq ID No 55 |
| GCAGCCAGCAAACTCC | 1275–1260 | Seq ID No 56 |
| GAGCGGGCAGTGTTGG | 1350–1334 | Seq ID No 57 |
| GAGTAGGCGCCATTGTGC | 1499–1482 | Seq ID No 58 |
| CTTGCAGGGTCAGCGAGTA | 1513–1495 | Seq ID No 59 |
| GGTGTTATGGTGGATGAGG | 1590–1572 | Seq ID No 60 |
| AGCTTGGTGCGGGTTCC | 1650–1634 | Seq ID No 61 |
| CCGGTTGGCAGTGTGGAG | 1671–1654 | Seq ID No 62 |
| CCTGGCATTCACATACTCC | 1848–1830 | Seq ID No 63 |
| AGGTCACTGAGCCATTCTG | 1900–1882 | Seq ID No 64 |
| GGAGAGGTCAGGTTTCACA | 2001–1983 | Seq ID No 65 |
| GAGTGGGTGCAGTTGATGG | 2072–2054 | Seq ID No 66 |
| CACCGCAGAGATGATGGAC | 2148–2130 | Seq ID No 67 |
| TGAGGATCCCAAAGACCAC | 2197–2179 | Seq ID No 68 |
| ATGCCCTTGTAGACTGTGC | 2387–2369 | Seq ID No 69 |
| AGCTGCACCGTGGATGTCA | 2561–2543 | Seq ID No 70 |
| GAGCCAGCCCGAAGTCT | 2776–2760 | Seq ID No 71 |
| CTTGGCCGACATTCAGAGT | 3077–3059 | Seq ID No 72 |
| TGGCCATGCGGGAGAAT | 3115–3099 | Seq ID No 73 |
| CAGTGAGCGGTAGAAGGTG | 3198–3180 | Seq ID No 74 |
| CGGTGCCTGTGGTGGAC | 3317–3301 | Seq ID No 75 |
| CATCTGGCTGGTTCACATA | 3607–3589 | Seq ID No 76 |
| TTGAAGGTGCTGGGTGGAG | 3887–3869 | Seq ID No 77 |
| TCAAGCAGGAAGGAAGGTT | 4099–4081 | Seq ID No 78 |

All probes are labelled with one or two fluorescein labels. As linkers, one or two NH$_2$CH$_2$CH$_2$(COCH$_2$OCH$_2$CON—(CH$_2$CH$_2$OCH$_3$)$_2$)CH$_2$COOH-linkers and/or one or two NH$_2$—(CH$_2$CH$_2$O)$_2$CH$_2$C(O)-linkers were used.

Another set of probes targeting the centromer of chromosome 17 was selected. These probes are included because the HER-2 gene in normal cells are located to chromosome 17, and aneuploidy is frequently observed in cancer cells. The nucleobase sequences of the peptide nucleic acid probes were as follows:

| AACGAATTATGGTCACAT | Seq ID No 73 |
| --- | --- |
| GGTGACGACTGAGTTTAA | Seq ID No 79 |

-continued

| | | |
|---|---|---|
| TTTGGACCACTCTGTGGC | Seq ID No 80 | |
| AACGGGATAACTGCACCT | Seq ID No 81 | |
| TTTGTGGTTTGTGGTGGA | Seq ID No 82 | |
| AGGGAATAGCTTCATAGA | Seq ID No 83 | |
| ATCACGAAGAAGGTTCTG | Seq ID No 84 | |
| CCGAAGATGTCTTTGGAA | Seq ID No 85 | |
| AAAGAGGTCTACATGTCC | Seq ID No 86 | |

All probes were labelled with one or two fluorescein labels. As linkers, one or two $NH_2CH_2CH_2(COCH_2OCH_2CON\text{—}(CH_2CH_2OCH_3)_2)CH_2COOH$-linkers and/or one or two $NH_2\text{—}(CH_2CH_2O)_2CH_2C(O)$-linkers were used.

The probes were synthesised according to standard PNA synthesis procedures.

Sample preparation, hybridisation, washing and detection are carried out as described above under Illustrative embodiment 2.

REFERENCES

1. WO 93/246252
2. WO 97/18325
3. DE 196 10 255
4. EP 727 487
5. EP 825 198
6. Tetrahedron Letters Vol. 36, No. 21, 3601–3604 (1995)
7. Tetrahedron Letters Vol. 35, No. 29, 5173–5176 (1994)
8. Nature 365, 566–568 (1993)
9. WO 95/17430

The invention claimed is:

1. A method of determining the presence or absence of chromosomal aberrations in a sample of eukaryotic origin comprising the steps of:
   a) contacting said sample with a hybridization solution comprising at least two sets of hybridization probes, at least one first set comprising one or more probes capable of hybridizing to specific nucleic acid sequences flanking one side of a potential breakpoint in a chromosome, and at least one second set comprising one or more probes capable of hybridizing to specific nucleic acid sequences flanking the other side of the potential breakpoint, wherein the first set of probes is labeled with at least one first specific label while the second set of probes is labeled with at least one second specific label different from the first specific label, and wherein the two sets of hybridization probes hybridize such that the first and second specific labels produce a fused signal if no chromosome break is present;
   b) removing any unbound and any non-specifically bound probe; and
   c) detecting the hybridized probes, and thereby determining the presence or absence of chromosomal aberrations in the sample.

2. A method according to claim 1 wherein each at least one set of hybridization probes comprises peptide nucleic acid probes containing from 8 to 40 polymerized moieties.

3. A method according to claim 1 wherein at least one set of hybridization probes comprises peptide nucleic acid probes comprising polymerized moieties of formula (I)

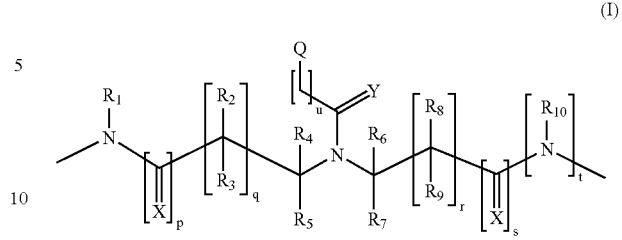

(I)

wherein
Y designates O or S,
each X independently designates O or S,
each Q independently designates a ligand that is selected from the group consisting of a naturally occurring nucleobase, a non-naturally occurring nucleobase, an intercalator, a nucleobase-binding group, a label and H,
u is an integer selected from the group consisting of 0, 1, 2, 3, 4, and 5,
p and s independently designate 0 or 1,
q and r independently designate 0 or 1,
t designates 0 or 1,
$R_1$ and $R_{10}$ independently designate H or $C_{1-4}$ alkyl,
$R_2$, $R_3$, $R_4$, $R_5$, $R_6$, $R_7$, $R_8$ and R9 are independently selected from the group consisting of H, the side chain of a naturally occurring amino acid, and the side chain of a non-naturally occurring amino acid.

4. A method according to claim 3, wherein t is 0, $R_1$ designates H or $CH_3$, and each of $R_3$, $R_4$, $R_6$, and $R_9$ designates H.

5. A method according to claim 3, wherein r is 0 and q and s are 1, and $R_1$ and $R_{10}$ independently designate H or $CH_3$.

6. A method according to claim 3, wherein p, r and t are 0, and wherein q and s are 1 and wherein $R_1$ is H.

7. A method according to claim 3, wherein the probe comprises polymerized moieties selected from the group consisting of formulas (IV)–(VI),

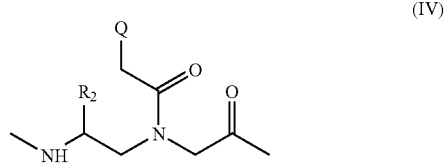

(IV)

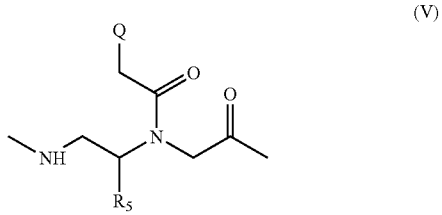

(V)

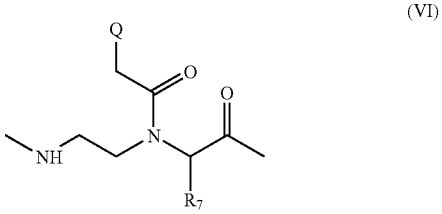

(VI)

wherein p, r, and t are 0, and u, s and q are 1, and wherein $R_1$ is H and wherein each Q is independently selected from the group consisting of a naturally occurring nucleobase, a non-naturally occurring nucleobase, an intercalator and a nucleobase-binding group.

8. A method according to claim 7, wherein $R_2$, $R_5$ and $R_7$ designate H or the side chain of amino acids selected from the group consisting of Ala, Asp, Cys, Glu, His, HomoCys, Lys, Orn, Ser and Thr, and wherein Q is selected from the group consisting of thymine, adenine, cytosine, guanine, uracil and hypoxanthine.

9. A method according to claim 3, wherein p, r, and t are 0, and u, s and q are 1 wherein $R_1$ is H, and wherein Q is selected from the group consisting of thymine, adenine, cytosine, guanine, uracil and hypoxanthine.

10. A method according to claim 7, wherein polymerized moieties of formulas (IV)–(VI) constitute at least 75% by weight of the probe.

11. A method according to claim 1, wherein each set of hybridization probes hybridizes within a genomic distance of no more than 100 kb.

12. A method according to claim 11, wherein each set of hybridization probes hybridizes within a genomic distance of no more than 50 kb.

13. A method according to claim 1, wherein at least one of the at least two sets of hybridization probes is a set of peptide nucleic acid probes.

14. A method according to claim 1, wherein the at least one first set of probes capable of hybridizing to specific nucleic acid sequences flanking one side of a potential breakpoint in a chromosome and the at least one second set of probes capable of hybridizing to specific nucleic acid sequences flanking the other side of the potential breakpoint are peptide nucleic acid probes.

15. A method according to claim 1, wherein the specific labels are chosen from fluorochromes.

16. A method according to claim 15, wherein the at least one first set of probes capable of hybridizing to specific nucleic acid sequences flanking one side of a potential breakpoint in a chromosome and the at least one second set of probes capable of hybridizing to specific nucleic acid sequences flanking the other side of the potential breakpoint are labeled with fluorochromes resulting in signals of comparable intensity between the sets of probes.

17. A method according to claim 1, further comprising a hybrid destabilizing agent in an amount effective to decrease the melting temperature of hybrids formed between said nucleic acid sequences and said probes so as to increase the ratio between specific and non-specific binding.

18. A method according to claim 17, wherein the hybrid destabilizing agent is selected from the group consisting of formamide, urea, guanidine, ethylene glycol, and glycerol.

19. A method according to claim 17, wherein the concentration of the hybrid destabilizing agent is above 10%.

* * * * *

UNITED STATES PATENT AND TRADEMARK OFFICE
CERTIFICATE OF CORRECTION

| | | |
|---|---|---|
| PATENT NO. | : 7,105,294 B2 | Page 1 of 1 |
| APPLICATION NO. | : 10/229110 | |
| DATED | : September 12, 2006 | |
| INVENTOR(S) | : Jacobus Johannus Maria Van Dongen et al. | |

It is certified that error appears in the above-identified patent and that said Letters Patent is hereby corrected as shown below:

On Title Page

Item (30) Foregn Application Priority Data should read --May 4, 1998 (DK) .... 00615/98-- and should be inserted below field (63) Related U.S. Application Data.

Signed and Sealed this

Twenty-first Day of November, 2006

JON W. DUDAS
*Director of the United States Patent and Trademark Office*